United States Patent
Wang et al.

(10) Patent No.: US 6,849,224 B2
(45) Date of Patent: *Feb. 1, 2005

(54) METHODS FOR PREPARING SELECTIVELY CROSS-LINKED POLYETHYLENE ORTHOPEDIC DEVICES

(75) Inventors: Aiguo Wang, Wood-Ridge, NJ (US); Aaron Paul Essner, Bloomingdale, NJ (US); Alfred J. Zarnowski, North Plainfield, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/094,789

(22) Filed: Mar. 11, 2002

(65) Prior Publication Data

US 2002/0100879 A1 Aug. 1, 2002

Related U.S. Application Data

(62) Division of application No. 09/553,503, filed on Apr. 20, 2000.
(60) Provisional application No. 60/130,322, filed on Apr. 21, 1999.

(51) Int. Cl.[7] .............................................. B29C 71/04
(52) U.S. Cl. ....................... 264/478; 264/485; 264/488; 264/494
(58) Field of Search .............................. 264/446, 488, 264/485, 494, 1.36, 85, 322, 328.1, 478

(56) References Cited

U.S. PATENT DOCUMENTS

| | | | |
|---|---|---|---|
| 2,904,480 A | 9/1959 | Rainer et al. | 204/154 |
| 3,022,543 A | 2/1962 | Baird, Jr. et al. | 18/57 |
| 3,057,791 A | 10/1962 | Anderson, Jr. | 204/154 |
| 3,090,770 A | 5/1963 | Gregorian | 260/45.5 |
| 3,162,623 A | 12/1964 | Cairns | 260/87.7 |

(List continued on next page.)

FOREIGN PATENT DOCUMENTS

| | | |
|---|---|---|
| EP | 0218003 AI | 4/1987 |
| EP | 0376503 AI | 7/1990 |
| EP | 0177552 B1 | 5/1992 |
| EP | 0 729 981 A1 | 9/1996 |
| EP | 1 065 034 A2 | 1/2001 |

(List continued on next page.)

OTHER PUBLICATIONS

B. Ranby, et al., Photodegradation, Photo–Oxidation and Photostabilization of Polymers, Principles and Applications, pp 60–71.

Robert M. Streicher, "Investigation on Sterilization and Modification of High Molecular Weight Polyethylenes by Ionizing Irradiation", Reprint from beta–gamma 1/89, beta–gamma 1/89, pp. 34–43.

(List continued on next page.)

Primary Examiner—Mathieu D. Vargot
(74) Attorney, Agent, or Firm—Lerner, David, Littenberg, Krumholz & Mentlik, LLP

(57) ABSTRACT

An improved prosthetic medical device having improved wear resistance and toughness is provided in the present application. A method is provided to selectively cross-link the polymeric matrix comprising the medical device by employing an interrupting means such as a mask, wire mesh or chopper wheel placed in between the medical device and irradiation source. In addition, the medical device may be translated while being irradiated to further effect the selective cross-linking. The present invention also provides for an injection molding process wherein a prosthetic medical device is formed in a single step, then selectively cross-linked.

20 Claims, 12 Drawing Sheets

Target radiated then rotated and radiated again

U.S. PATENT DOCUMENTS

| | | | |
|---|---|---|---|
| 3,297,641 A | 1/1967 | Werber et al. | 260/66 |
| 3,330,748 A | 7/1967 | Lawton | 204/158 |
| 3,352,818 A | 11/1967 | Meyer et al. | 260/45.7 |
| 3,563,869 A | 2/1971 | Rainer et al. | 204/159.2 |
| 3,616,365 A | 10/1971 | Stastny | 204/159.14 |
| 3,758,273 A | 9/1973 | Johnston et al. | 21/54 |
| 3,832,827 A | 9/1974 | Lemelson | 53/111 R |
| 3,886,056 A | 5/1975 | Kitamaru et al. | 204/159.2 |
| 4,226,905 A | 10/1980 | Harbourne | 428/220 |
| 4,587,163 A | 5/1986 | Zachariades | 428/292 |
| 4,655,769 A | 4/1987 | Zachariades | 623/1 |
| 4,701,288 A | 10/1987 | Cook et al. | |
| 4,813,210 A | 3/1989 | Masuda et al. | 53/425 |
| 4,820,466 A | 4/1989 | Zachariades | 264/119 |
| 4,832,965 A | 5/1989 | Helin | 426/66 |
| 4,950,151 A | 8/1990 | Zachariades | 425/379.1 |
| 5,030,402 A | 7/1991 | Zachariades | 264/138 |
| 5,037,928 A | 8/1991 | Li et al. | 526/352 |
| 5,096,654 A | 3/1992 | Craggs et al. | 264/570 |
| 5,153,039 A | 10/1992 | Porter et al. | 428/36 |
| 5,160,464 A | 11/1992 | Ward et al. | 264/22 |
| 5,160,677 A | 11/1992 | Gravener et al. | |
| 5,222,949 A | 6/1993 | Kaldany | |
| 5,414,049 A | 5/1995 | Sun et al. | 525/333.7 |
| 5,508,319 A | 4/1996 | DeNicola, Jr. et al. | 522/161 |
| 5,728,510 A | 3/1998 | White | 430/323 |
| 5,814,423 A | 9/1998 | Maruyama et al. | 430/5 |
| 5,879,400 A | 3/1999 | Merrill et al. | 623/22 |
| 6,017,975 A | 1/2000 | Saum et al. | 522/161 |
| 6,090,527 A | 7/2000 | Yamazaki et al. | |
| 6,165,220 A | 12/2000 | McKellop et al. | |
| 6,365,089 B1 | 4/2002 | Krebs et al. | |
| 6,372,256 B2 | 4/2002 | Jamiolkowski et al. | |

FOREIGN PATENT DOCUMENTS

| | | |
|---|---|---|
| EP | 1 072 275 A1 | 1/2001 |
| GB | 2060469 B | 9/1983 |
| GB | 2180815 | 4/1987 |
| GB | 2156733 B | 10/1987 |
| GB | 2157298 B | 11/1987 |
| GB | 2225551 A | 6/1990 |
| GB | 2207436 B | 7/1991 |
| JP | 59-71830 | 4/1984 |
| WO | 9011060 | 11/1990 |

OTHER PUBLICATIONS

Robert M. Streicher, "Ionizing irradiation for sterilization and modification of high molecular weight polyethylenes*", *Plastics and Rubber Processing and Applications*, vol. 10, No. 4, 1988, pp. 221–229.

R.M. Streicher, "Influence of Ionizing Irradiation in Air and Nitrogen for Sterilization of Surgical Grade Polyethylene for Implants", *Radiat. Phys. Chem.*, vol. 31, Nos. 4–6, pp. 693–698, 1988.

R.M. Streicher, Change in Properties of High Molecular Weight Polyethylenes After Ionizing Irradiation for Sterilization and Modification, *Radiation processing for plastics and rubber III*, Department of Medical Engineering, Sulzer Brothers Ltd., Winterthur, Switzerland.

R.M. Streicher, "Improving UHMWPE By Ionizing Irradiation Crosslinking During Sterilization", Sulzermedica, Department of Medical Engineering, Winterthur, Switzerland, 17th Annual Meeting of the Society of Biomaterials, May 1–5, 1991.

D.J. Dijkstra et al., Cross–linking of ultra–high molecular weight polyethylene in the melt by means of electron beam irradiation, *Polymer*, 1989, vol. 30, May, pp. 866–770.

R.M. Streicher, "The Behavior of UHMW–PE when Subjected to Sterilization by Ionizing Radiation", *Ultra high molecular weight polyethylene as biomaterial in orthopedic surgery*, pp. 66–73,1991.

H.Y. Kang, et al., "The Radiation Chemistry of Polyethylene. IX. Temperature Coefficient of Cross–Linking and Other Effects[1]", *Journal of the American Chemical Society*/ 89.9/Apr. 26, 1967, pp. 1980–1986.

Masaru Matsuo, et al., "Cross–Linking of Ultrahigh Molecular Weight Polyethylene Films Produced by Gelation/Crystallization form Solution under Elongation Process", *Macromolecules*, vol. 19, No. 7, Jul. 1986, pp. 2028–2035.

D.J. Dijkstra, et al. "Cross–linking of porous gel–spun ultra–high molecular weight polyethylene by means of electron beam irradiation", Polymer Bulletin, vol. 20, pp. 557–582, (1988).

D.J. Dijkstra, et al. "Cross–linking of porous gel–spun ultra–high strength polyethylene fibers by means of electron beam irradiation", *Polymer Bulletin*, vol. 17, pp. 507–513, (1987).

W.G. Perkins, et al., "Effect of Gamma Radiation and Annealing on Ultra–Oriented Polyethylene", *Polymer Engineering and Science*, Mid–May, 1978, vol. 18, No. 6, pp. 527–532.

Junkichi Sohma, "Radical Migration as an Elementary Process in Degradation", vol. 55, No. 10, pp. 1595–1601, 1983.

D.A. Blackadder, et al., "Properties of polymer crystal aggregates. (2) Annealing of polyethylene crystal aggregates", pp. 147–164, 1969.

Akeharu Tsuruta et al., "Annealing of Ultra–Oriented High Density Polyethylene Extrudates", *Polymer Engineering and Science*, Jun. 1983, vol. 23, No. 9, pp. 521–529.

C. Sawatari, et al., "Temperature–dependence of mechanical and morphological properties of ultra–high molecular weight polyethylene cross–linked by electron beam irradiation", *Colloid & Polymer Science*, vol. 226, No. 4 (1988), pp. 316–323.

M. Narkis, et al., "Structure and Tensile Behavior of Irradiation– and Peroxide– Crosslinked Polyethylenes", *Journal of Macromolecular Science—Physics*, vol. B26, No. 1, 1987, pp. 37–58.

Harold Schonhorn, et al., "Surface Crosslinking of Polyethylene and Adhesive Joint Strength", *Journal of Applied Polymer Science*, vol. 18, pp. 235–243 (1974).

L. Minkova, et al., Blends of normal high density and ultra–high molecular weight polyethylene, γ irradiated a at a low dose, *Colloid Polymer Science*, vol. 268, No. 11, pp. 1018–1023 (1990).

C.T. Lue, et al., "Approaching the Properties of UHMW–PE by Crosslinking Low Molecular Weight HDPE", *ANTEC '84*, pp. 538–541 (1984).

M.S. Jahan, et al., "Combined Chemical and Mechanical Effects on Free Radicals in UHMWPE Joints During Implantation", *Journal of Biochemical Materials Research*, vol. 25, pp. 1005–1017, (1991).

Patel, et al., "Crystallinity and the Effect of Ionizing Radiation in Polyethylene. I. Crosslinking and Crystal Core; II. Crosslinking in Chain–Folded Single Crystals; III. An Experiment on the Irradiation–Induced Crosslinking in n–Hexatriacontane", *Journal of Polymer Science: Polymer Physics Edition*, vol. 13, pp. 303–338, (1975).

Yoshihiro Sakai, et al., Effect of electron beam irradiation on simultaneously biaxially drawn ultra–high molecular weight polyethylene dried gel films, *POLYMER*, 1993, vol. 34, No. 16, pp. 3362–3345.

Francis Cracco, et al., "ESR Studied of Free Radical Decay in Irradiated Polyethylene", *The Journal of Chemical Physics*, vol. 37, No. 10, Nov. 15, 1962, pp. 2449–2457.

C.J. Grobbelaar, et al., "The Radiation Improvement of Polyethylene Prostheses", *The Journal of Bone and Joint Surgery*, vol. 60–B, No. 3, Aug. 1978, pp. 370–374.

A. Charlesby, "The effects of ionising radiation on polymers", *Irradiation Effects on Polymers*, pp. 49–59, 1991.

R.A. Jones et al., "Radiation–Induced Crosslinking of Polyethylene in the Presence of Acetylene: A Gel Fraction, UV–Visible, and ESR Spectroscopy Study", *Journal of Polymer Science: Part B: Polymer Physics*, vol. 31, pp. 807–819 (1993).

S. Shimada et al., "Relation between diffusion controlled decay of radicals and $\chi$–relaxation in polyethylene and polyoxymethylene", *Polymer*, vol. 20, 404 (1979).

M.S. Jahan et al., "Effect of Post–Irradiation Storage Condition on Thermoluminescence From Ultra–High Molecular Weight Polyethlene", *Journal of Luminescence*, 40 & 41 (1988), pp. 242–243.

M. Gvozdic et al., "Kinetics of Free Radical Decay Reactions in Irradiated Isotactic Polypropylene", *The Journal of Physical Chemistry*, vol. 85, No. 11, 1981, pp. 1563–1569.

M. Gvozdic et al., "Kinetics of Free Radical Decay Reactions in Irradiated Isotactic Polypropylene", *The Journal of Physical Chemistry*, vol. 85, No. 11, 1981, pp. 1563–1569.

D.A. Blackadder et al., "Annealing of high density polyethylene for very long times at low supercooling under vacuum", *Polymer*, 1972, vol. 13, Dec., pp. 584–586.

J. de Boer et al., "Crosslinking of ultra–high molecular weight polyethylene in the oriented state with dicumylperoxide", *Polymer*, 1984, vol. 25, Apr., pp. 513–519.

Chris Saunders et al., "Radiation Effects on Microorganisms and Polymers for Medical Products", *Radiation Effects on Polymers*, pp. 89–92, 1991.

Shigetaka Shimada et al., "Free radicals trapped in polyethylene matrix: 2. Decay in single crystals and diffusion", *Polymer*, vol. 18, No. 25, (1977).

T.F. Williams et al., "Physical and Inorganic Chemistry", *Journal of the American Chemical Society*, vol. 81, No. 12, Jul. 2, 1959, pp. 2919–2926.

D.J. Carlsson et al, "Polypropylene Degradation by $\gamma$–Irradiation in Air", *Polymer Stabilization and Degradation*, pp. 359–371, 1985.

H. Kashiwabara, "ESR Application to Radiation Chemistry of Polymers", *Radiat. Phys. Chem.*, vol. 32, No. 2, pp. 203–208, 1988.

Marylyn Bakker, Editor–in–chief, *The Wiley Encyclopedia of Packaging Technology*, 1986, pp. 530, 562, 564.

D.C. Waterman et al., "The Radiation Chemistry of Polyethylene. X. Kinetics of the Conversion of Alkyl to Allyl Free Radicals", *The Radiation Chemistry of Polyethylene*, vol. 74, No. 9, Apr. 30, 1970, pp. 1913–1922.

Martin Hudis, "Surface Crosslinking of Polyethylene Using a Hydrogen Glow Discharge", *Journal of Applied Polymer Science*, vol. 16, pp. 2397–2415 (1972).

Martin Hudis, "Surface Crosslinking of Polyethylene Using a Hydrogen Glow Discharge", *Journal of Applied Polymer Science*, vol. 16, pp. 2397–2415 (1972).

Jonathan Black, Ph.D., *Orthopaedic Biomaterials in Research and Practice*, pp. 144–150, 1988.

Fred W. Billmeyer, Jr., *Textbook of Polymer Science*, $3^{rd}$ Edition, pp. 312–314, 1984.

Ferdinand Rodriguez, *Principles of Polymer Systems*, Second Edition, pp. 216–218, 1982.

H. Miyaji et al., "Annealing of nodular linear polyethylene crystallized fom the glass", *Polymer*, 1981, vol. 22, May, pp. 701–703.

R. Kitamaru et al., "Irradiation Cross Linking of Polyethylene. The Temperature Dependence of Cross Linking in the Crystalline and Amorphous States[1] ", *Journal of the American Chemical Society*, vol. 86, pp. 3529–3534 (1964).

"Radical Migraton as an Elementary Process in Degradation" Pure & Applied Chem.; vol. 55 No. 10, pp. 1595–1601, 1983.

Combined Chemical and Mechanical Effects on Free Radicals in UHMWPE Joints During Implantation, Jnl. Biomed. Matec Research, vol. 25, 1991.

"Polypropylene Degradation by 2–Irradiation in Air", American Chemical Society, 1985, pp. 359–371.

"Radiation Effects on Polymers", American Chemical Society 1991. (Symposium of Aug. 26–31, 1990) pp. 89–92.

Cup

Cup

Knee

Knee

METHODS FOR PREPARING SELECTIVELY CROSS-LINKED POLYETHYLENE ORTHOPEDIC DEVICES

CROSS REFERENCE

This is a divisional application of U.S. patent application Ser. No. 09/553,503, filed Apr. 20, 2000, entitled SELECTIVELY CROSS-LINKED POLYETHYLENE ORTHOPEDIC DEVICES, which claims the benefit of Provisional Application 60/130,322, filed Apr. 21, 1999. The contents of these applications are hereby incorporated by reference in their entirety.

FIELD OF THE INVENTION

This invention relates generally to producing prosthetic medical devices. More specifically, the invention provides methods to produce compositions made of polyethylene which have been irradiated in such a manner so that only a selected percentage of the overall composition has been allowed to cross-link. The capability to precisely control the degree and location of cross-linking in a polymer has particular advantages in the orthopedic device arts.

BACKGROUND OF THE INVENTION

Many prosthetic medical devices are implanted into load-bearing joints such as knees, hips, etc. As such, these prosthetic devices must be very strong and possess a high degree of wear resistance. The prosthetic medical device industry has utilized various methods and compositions employing metals and polymers and combinations thereof to fabricate prosthetic devices. Prosthetic medical devices manufacturers constantly work toward developing better products by improving their physical properties. Improved wear resistance, for example, is a desirable quality to impart to a prosthetic medical device. Improving wear resistance without losing strength or causing oxidative degradation is a difficult balance to obtain.

Various methods of manufacturing compositions of polymeric materials have been devised with the objectives of reducing wear rate and improving the oxidation resistance of the polymeric materials used to fabricate prosthetic medical devices. U.S. Pat. Nos. 6,017,975, 5,879,400, 5,414,049 and 5,728,510 are referenced herein to illustrate the common methods and compositions used to fabricate polymeric prosthetic devices presently employed in the field.

One common practice within the prosthetic medical device industry is to use cross-linked polymers and resins to form the medical device. "Cross-linked" polymers are defined as polymeric materials which have been subjected to chemical or radiation-initiated activation resulting in dendritic bond formation between and amongst individual polymeric chains yielding new intermolecular and intramolecular networks. These cross-linked networks within the polymer provide chemical and physical properties which are usually different from the virgin polymer. Such properties include increased wear and creep resistance, durability, etc. Indiscriminate or uncontrolled cross-linking of the polymeric material comprising the prosthetic device may result in improved wear resistance, but strength and other desirable properties may be sacrificed.

Another difficulty conventionally encountered in the manufacturing process of polymeric components of ball and socket or bearing-type prosthetic medical devices, such as hips, knees, and other load-bearing joints, is that they cannot be formed easily by inexpensive injection molding techniques. Instead, these particular types of prostheses must first be formed into a stock bar or rod, by extrusion for example, after which further machining is necessary to form the finished article. Injection molding, on-the-other-hand, allows for the final article to be formed in virtually one step.

Therefore, a need exists within the prosthetic medical device industry to fabricate an improved polymeric prosthetic device possessing sufficient strength to withstand the stress and pressure imposed on it, yet resist wear. There also exists a need to fabricate the devices inexpensively by injection molding. The present invention provides compositions, as well as methods of improving the wear resistance of prosthetic medical devices, by selectively cross-linking a polymeric resin using a controlled cross-linking process providing improved strength and wear resistance.

The present invention also provides compositions and methods of injection molding and selectively cross-linking prosthetic medical devices thus rendering an inexpensive, and more facile prosthetic medical device fabrication process.

SUMMARY OF THE INVENTION

The present invention provides methods of producing selectively cross-linked polyethylene orthopedic devices. Specifically, the invention provides a localized and controlled cross-linking method used to produce orthopedic implant prosthesis having improved wear characteristics. The localized and controlled degree of cross-linking is accomplished by exposing a polyethylene object or preformed orthopedic prosthetic joint or limb bearing surface to an interrupted, masked or pulsed radiation source. The interrupted radiation source may be accomplished by various means, all of which limit the amount of radiation ultimately contacting the object. By interrupting or limiting the radiation exposure to certain sites on the polyethylene object or prosthetic device, cross-linking only occurs where the radiation is able to contact or penetrate the object. Other areas not so contacted with the radiation either do not become cross-linked or only peripherally so. The invention therefore, allows a technician not only to control where the cross-linking will take place within or on the surface of a workpiece, but also the degree to which the polymer ultimately becomes cross-linked. By limiting or selectively cross-linking the polymeric device, one can impart specific desirable properties to the polymer not normally present in the raw polymer or in the fully cross-linked polymer of the prior art.

It is therefore one aspect of the invention to provide a process for preparing an orthopedic device by preferably providing a polyethylene workpiece such as a stock bar or rod, or alternatively, a pre-formed joint or limb bearing. The polyethylene workpiece is then positioned in the path of a radiation beam. Preferably, a beam interrupter is placed between the workpiece and the beam source. The radiation source is then activated so that the beam is cast toward the workpiece but preferably interrupted partially by the interrupting means. The workpiece is preferably exposed to the interrupted radiation beam for a certain amount of time known to produce the desired amount of cross-linking. The degree of cross-linking imparted to the workpiece may correspond to a specific degree of mechanical toughness and wear resistance in the finished prosthesis.

The present invention provides for the fabrication of various types of prosthetic devices. While the invention is not limited to any particularly shaped prosthetic device, the preferred shapes include acetabular cups, knees, ankles, shoulders, tibial and femoral joints, finger and thumb members, vertebra, elbows, foot and toe members and wrist members.

In another aspect of the invention the polymeric materials used to form the prosthetic device may selected from the group of polyethylenes including, but not limited to, high molecular weight polyethylene (HMWPE), ultra high molecular weight polyethylene (UHMWPE), high density polyethylene (HDPE), ultra high density polyethylene (UHDPE), cross-linked polyethylene and non-cross-linked polyethylene. In this aspect of the present invention, any combination of polymers listed above, or their equivalents, may be used. A preferred polymer of the invention is UHMWPE, and a preferred combination is UHMWPE and HDPE.

It is another aspect of the invention to provide a mask, shield or screen to serve as the interrupting means. The mask may preferably be a perforated sheet preferably made of metal, graphite or other thermally stable equivalent material. The number of perforations would preferably correspond to the ultimate exposure, and therefore the cross-linking of the workpiece. Another interrupting means may preferably be a wire mesh which would also limit the amount of radiation ultimately reaching the workpiece depending on the mesh size of the sheet. It is preferable to practice the present invention with individual interrupting devices, however, any combination may be used.

It is another aspect of the present invention to provide a curved interrupting means, preferably a perforated sheet or wire mesh sheet. The curved sheet or mask may partially or completely surround the workpiece but in either case provide partial shielding of the radiation beam to the workpiece, and thus serve as an interrupting means. The curved sheet or mask may be contoured to match the surface of a prepared polymeric workpiece or preformed prosthetic device such as, for example, an acetabular cup or tibial member.

Yet another aspect of the present invention is to provide a rotating chopper wheel serving to interrupt the beam intermittently, thereby introducing cross-linking to specific areas or regions of the workpiece.

Another object of the invention is to provide a pulsed radiation beam, thereby limiting the degree of radiation ultimately contacting the workpiece.

The present invention also provides a method of irradiating a workpiece using a plurality of radiation sources. The radiation sources may preferably be directed in the same or different directions, all contacting the workpiece.

It is yet another aspect of the invention to provide a method whereby the workpiece is preferably completely surrounded by an interrupting means, preferably a perforated cage, whereby a preferably plurality of radiation sources are directed to the workpiece from various directions to provide an all-encompassing and uniform radiation exposure to the workpiece.

It is yet another aspect of the invention to rotate or otherwise translate the workpiece while it is exposed to the interrupted radiation beam.

In another aspect of the invention, the workpiece and/or the interrupting means such as a perforated mask or wire mesh is vibrated while in the path of the radiation beam.

It is yet another aspect of the invention to form a prosthetic device or pre-formed article by injection molding which is suitable for ball and socket and bearing-type prosthetic joints.

DETAILED DESCRIPTION OF THE PRESENT INVENTION

Figure 1:
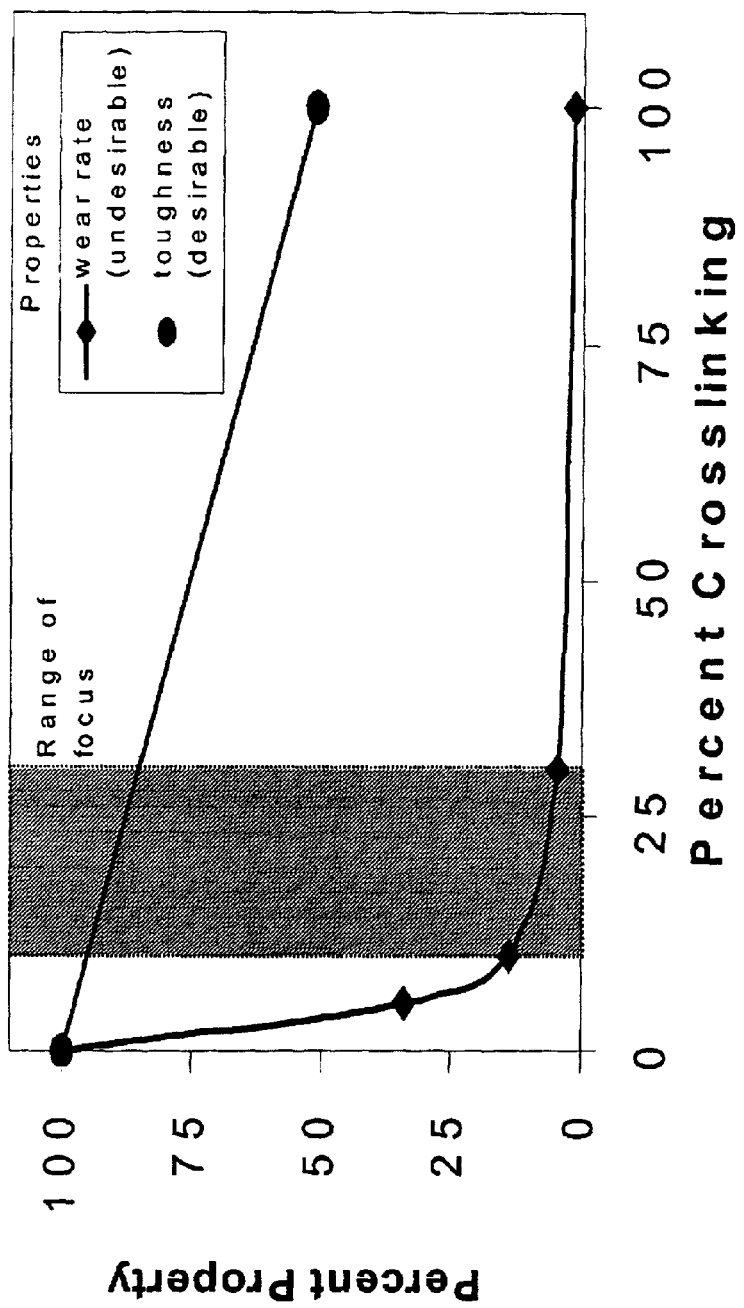
FIG. 1 depicts a graphic representation of the effects of selective cross-linking polyethylene on wear rate and toughness.

The present invention provides a desirable balance of improved wear resistance and high tensile strength and toughness in the polymeric compositions used for prosthetic implants. It has been discovered that wear resistance can be improved without sacrificing other desirable properties such as toughness or strength by controlling the amount of cross-linking of the polymeric substrate comprising the prosthetic device. Referring to FIG. 1, whereby the wear rate and toughness are graphically illustrated to be optimized at about 5 to 30% cross-linking. The present invention also provides that not only is the degree of controlled cross-linking useful in providing the desired properties, but also the localized positioning of the cross-linked phase of the polymer within the matrix. Thus, the above noted percentage of cross-linking may be distributed uniformly over the entire surface area, and/or within the matrix, of the workpiece, or may comprise a specific pattern of cross-linking, depending upon the ultimate use of the finished prosthetic device.

The practice of the present invention has resulted in improved wear reduction with less loss of mechanical properties, as compared to bulk cross-linked prosthetic devices. Thus the essence of the present invention is to control the degree and location of the cross-linked phase of the polymer within the matrix of the prosthetic device or stock work piece which results in a desirable balance of properties between wear resistance and toughness.

Figure 9:
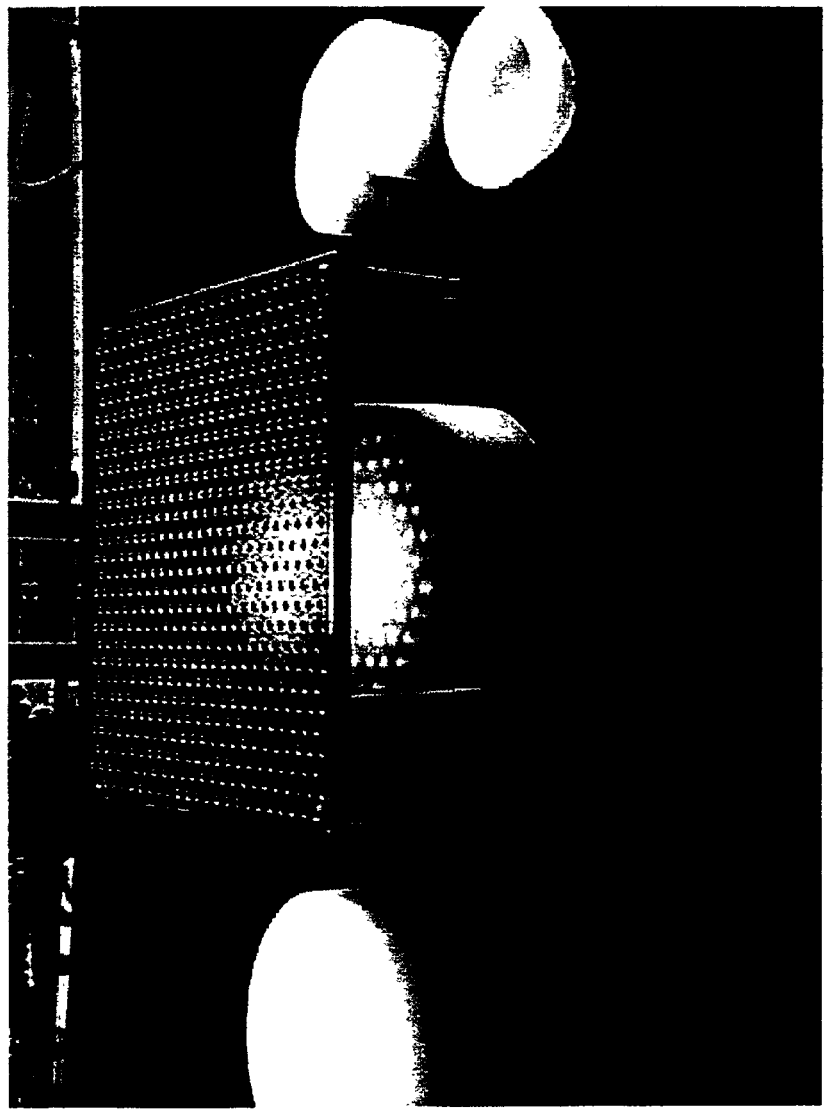
FIG. 9 depicts a workpiece positioned under a perforated mask or shield whereby a visible light is shown to demonstrate the path and pattern of a radiation beam during operation of the present invention.

This balance, and therefore the polymeric selectivity in cross-linking, of the present invention is achieved by virtue of interrupted irradiation exposure of the polyethylene article to effectuate a selected pattern and percentage of cross-linking in the article being treated. This process is termed "selective cross-linking." As will be described in detail below, the interruption in the irradiation exposure of the work piece is accomplished by various means. For illustrative purposes, such means may preferably be a perforated mask, wire mesh, chopper wheel, or other device capable of partially blocking the path of the radiation beam. See FIG. 9 whereby a workpiece is positioned under a perforated mask or shield. A light is projected onto the upper surface of the mask to demonstrate the interrupted path of what the radiation beam would contact as well as the penetration pattern projected onto the workpiece. In other examples, the beam may be interrupted by pulsing the emission of the beam from the source, as well as projecting a finely focused beam, or a plurality of such, directly onto the work piece. In addition, the dose, or exposure time, of the irradiation can be varied separately or in conjunction with the use of the above-described interruption means to provide another method of controlling the level of cross-linking. For the purposes of describing the present invention, "percent cross-linking" means the fraction of overall radiation energy projected toward the workpiece which is not interrupted and thus ultimately contacts the workpiece.

Figure 8:
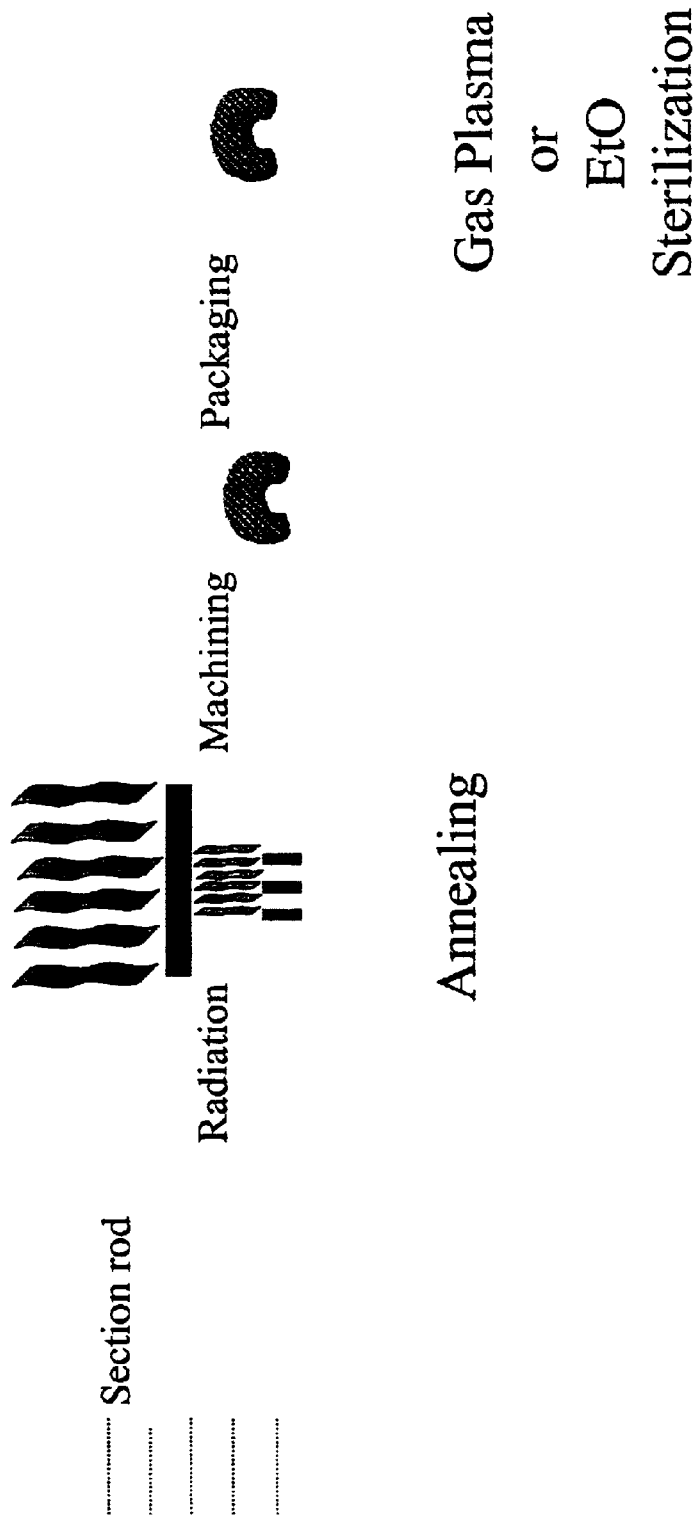
FIG. 8 depicts a representation of the general process of fabricating a prosthetic medical device according to the present invention.

Generally, to practice the present invention, a polymer workpiece is placed in the path of, or adjacent to, an irradiation beam, the beam is interrupted by an interrupting means for a desired period of time to effectuate the desired level of cross-linking. The workpiece is then annealed. Thereafter, the workpiece is shaped into a prosthetic device as necessary and packaged according to common industry processes. See FIG. 8 for a schematic representation of a typical method of processing a prosthetic device according tot he present invention. The processing of the prosthetic device, after selectively cross-linking according to the present invention, may be performed by conventional methods. For example the necessary packaging, finishing, annealing, sterilizing, etc. may be practiced according to those processes disclosed and/or claimed in U.S. Pat. No. 5,414,049, which is hereby incorporated by reference.

Figure 3:
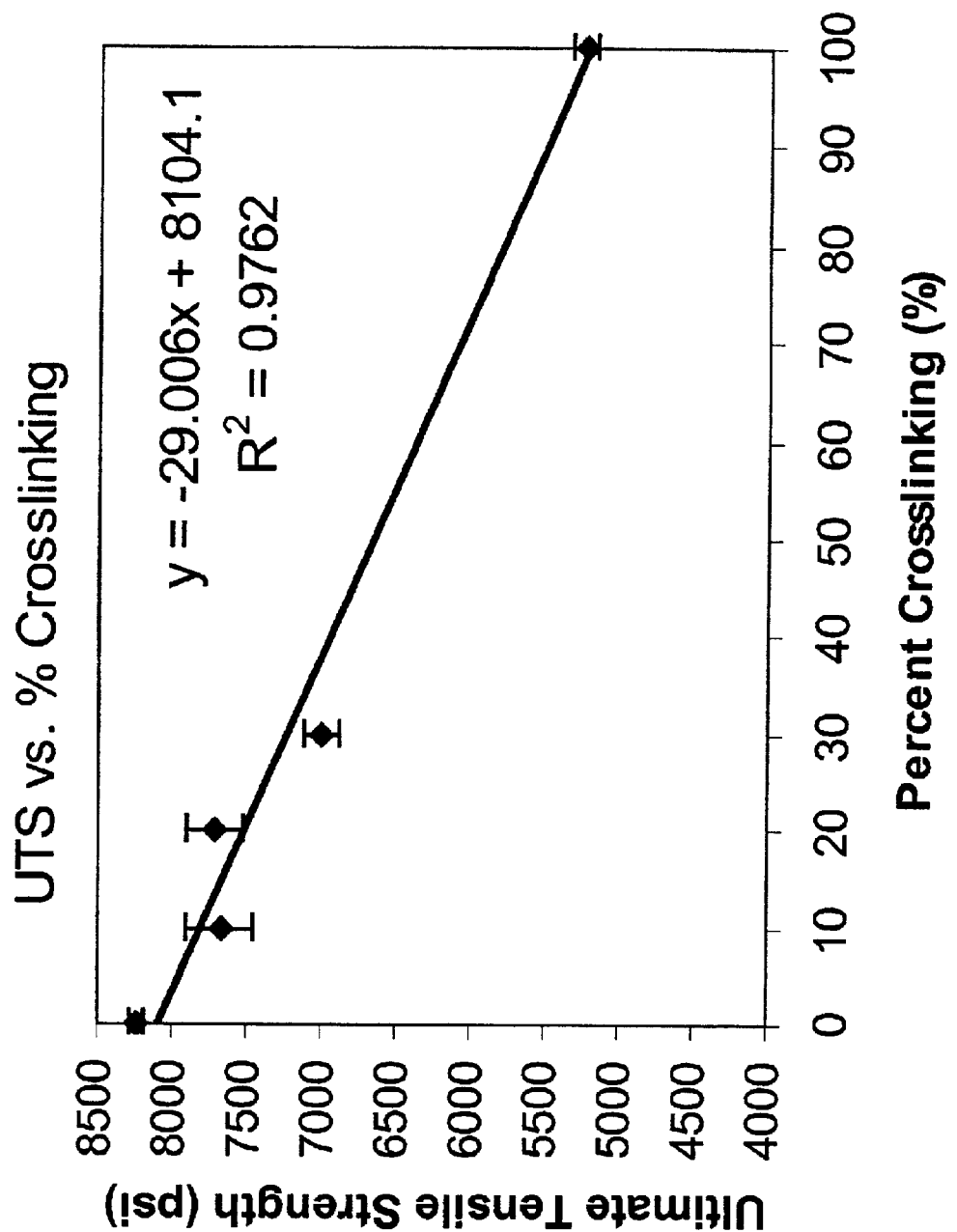
FIG. 3 depicts a representation of ultimate tensile strength versus percent cross-linking.
Figure 4:
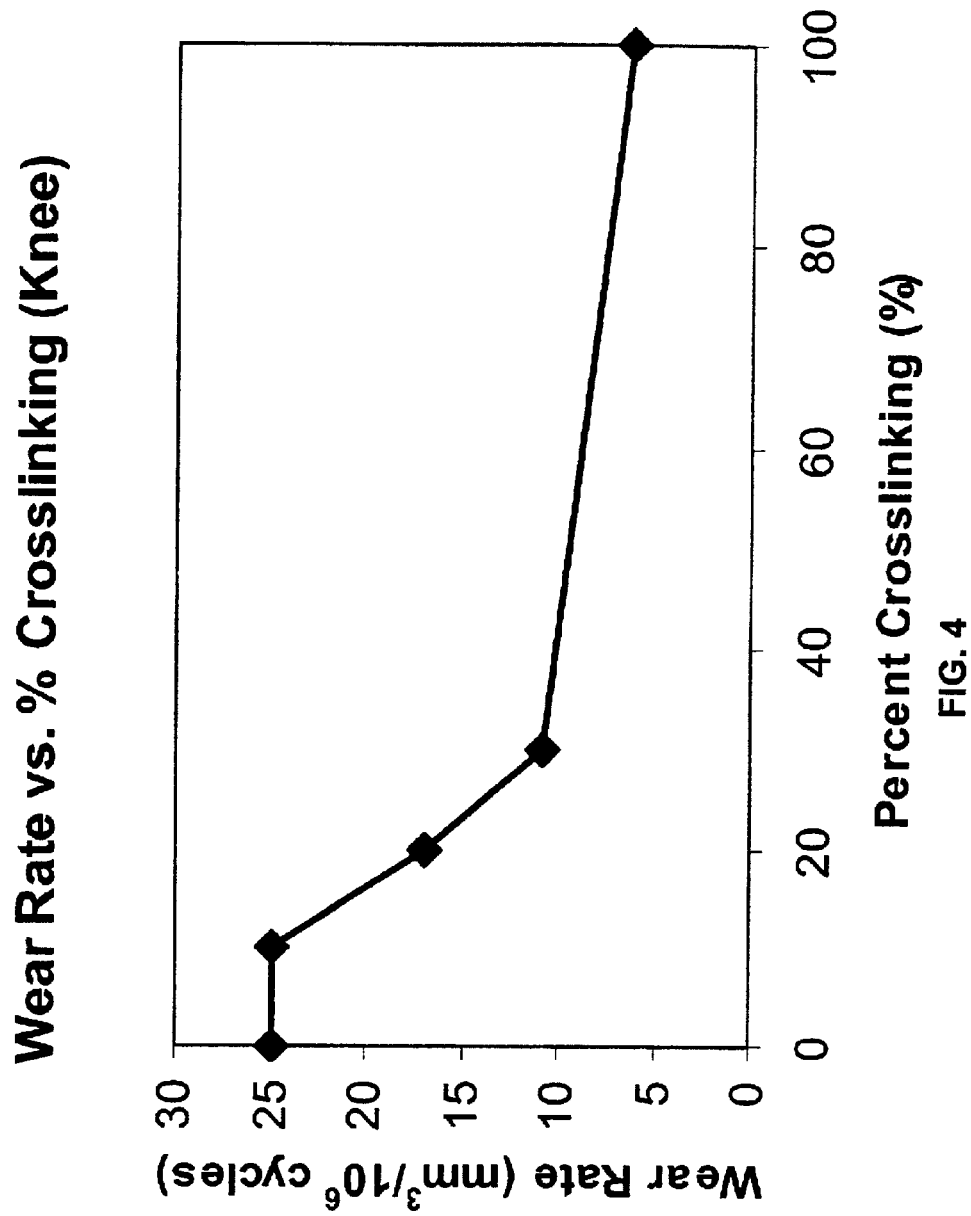
FIG. 4 depicts a representation of knee wear rate versus percent cross-linking.
Figure 5:
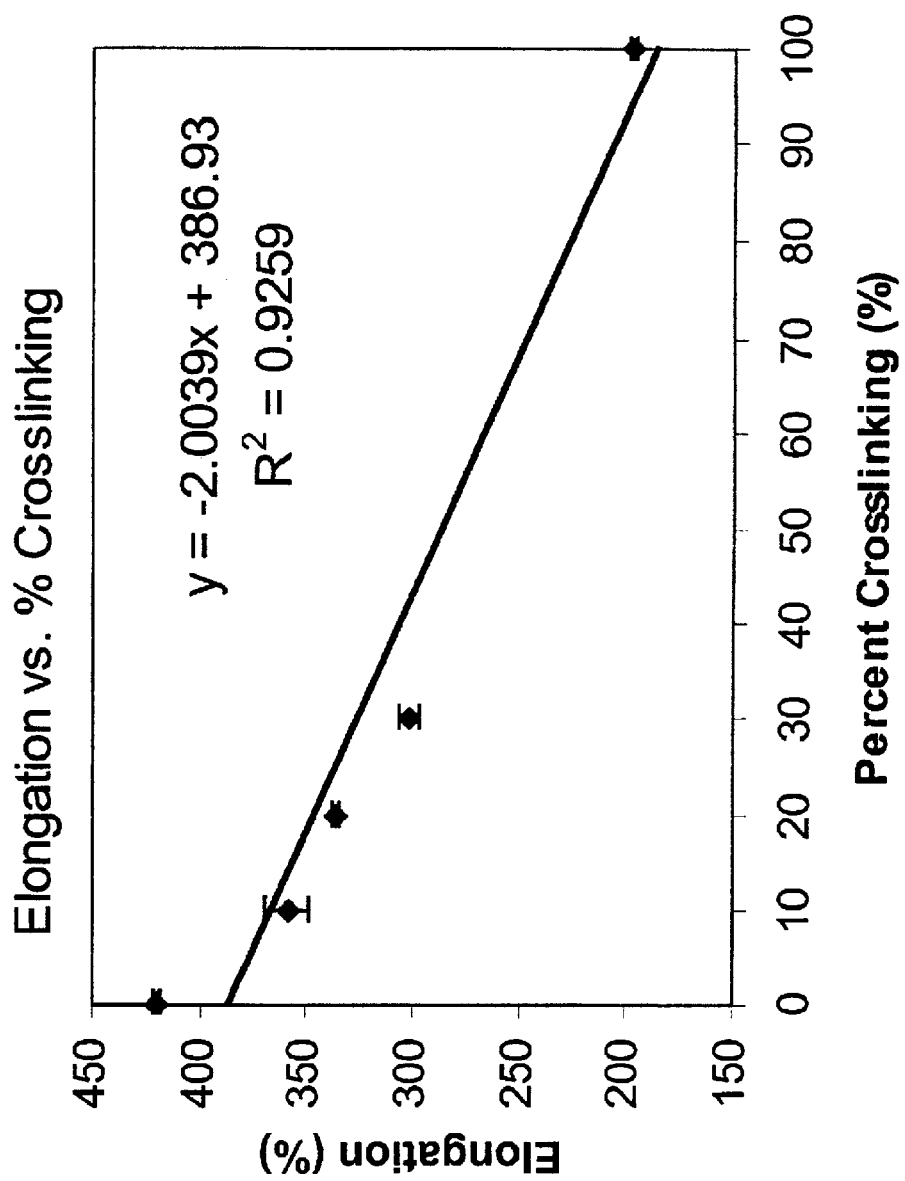
FIG. 5 depicts a representation of elongation versus percent cross-linking.

Prosthetic devices fabricated according to the present invention possess an improved performance profile as compared to control devices comprising 100% cross-linking. For example FIG. 3 plots ultimate tensile strength versus percent cross-linking. As illustrated, devices possessing 10, 20 and 30% cross-linking exhibit low levels of strength loss as compared to the control. However, FIG. 4 illustrates a desirable decrease in wear rate at the same 10, 20 and 30% cross-linking levels. In addition, FIG. 5 illustrates a minimum change of elongation, at 10, 20 and 30% cross-linking as compared to the control which is 100% cross-linked. The above data demonstrates that the selective cross-linking of the present invention provides a balance of desirable properties such as low wear rate and high mechanical toughness without the undesirable properties such as brittleness and accelerated wear rates.

Regardless of the method or device used, the present invention provides for any controlled and/or selective exposure of the work piece to a radiation beam for the purposes of limiting the degree of cross-linking within the polymeric matrix of the prosthetic device or preformed work piece. Note that the dose or exposure time of the radiation beam contributes to the overall properties of the prosthetic devices of the present invention.

Figure 6:
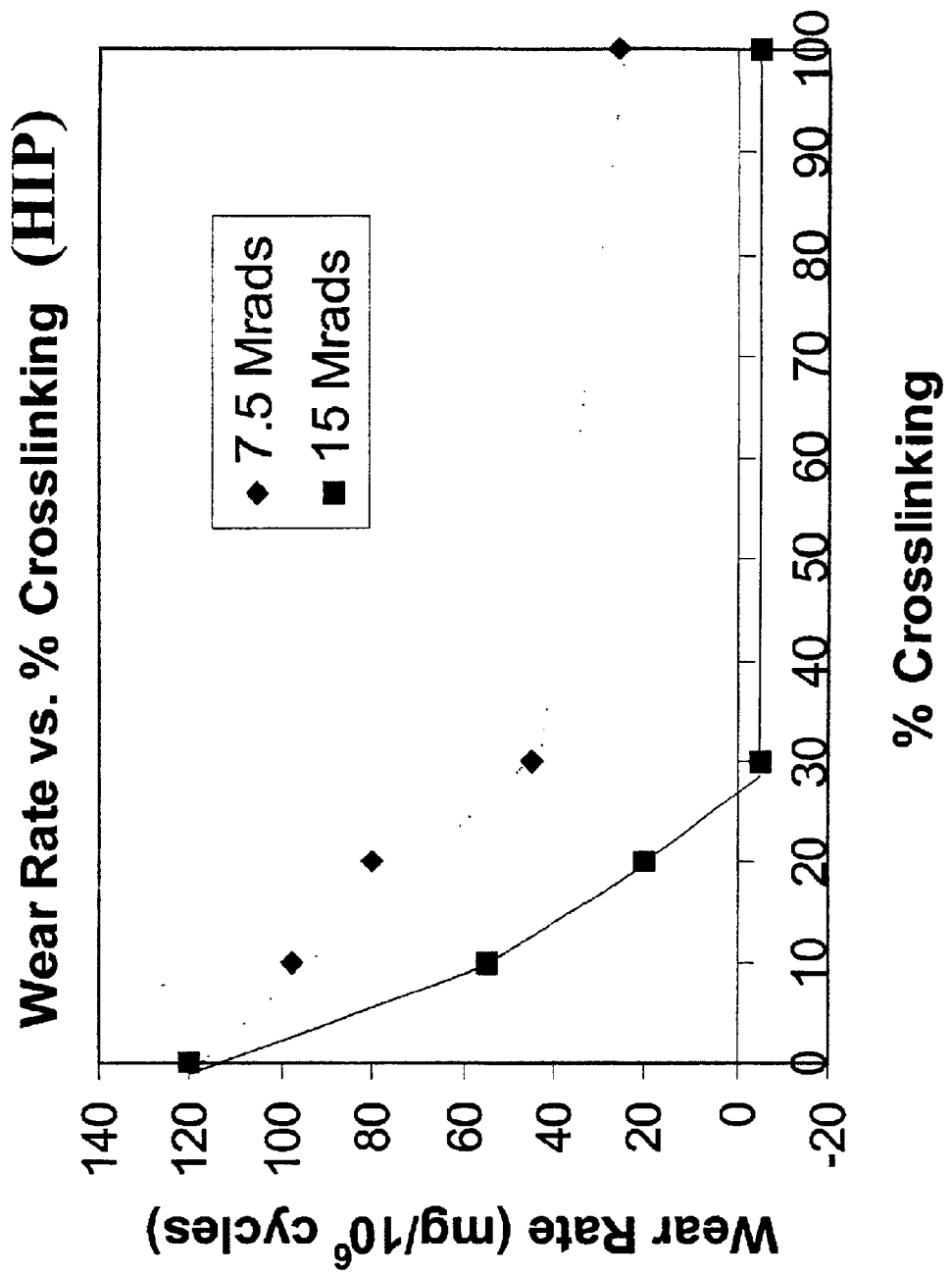
FIG. 6 depicts a representation of hip wear rate versus percent cross-linking.
Figure 7:
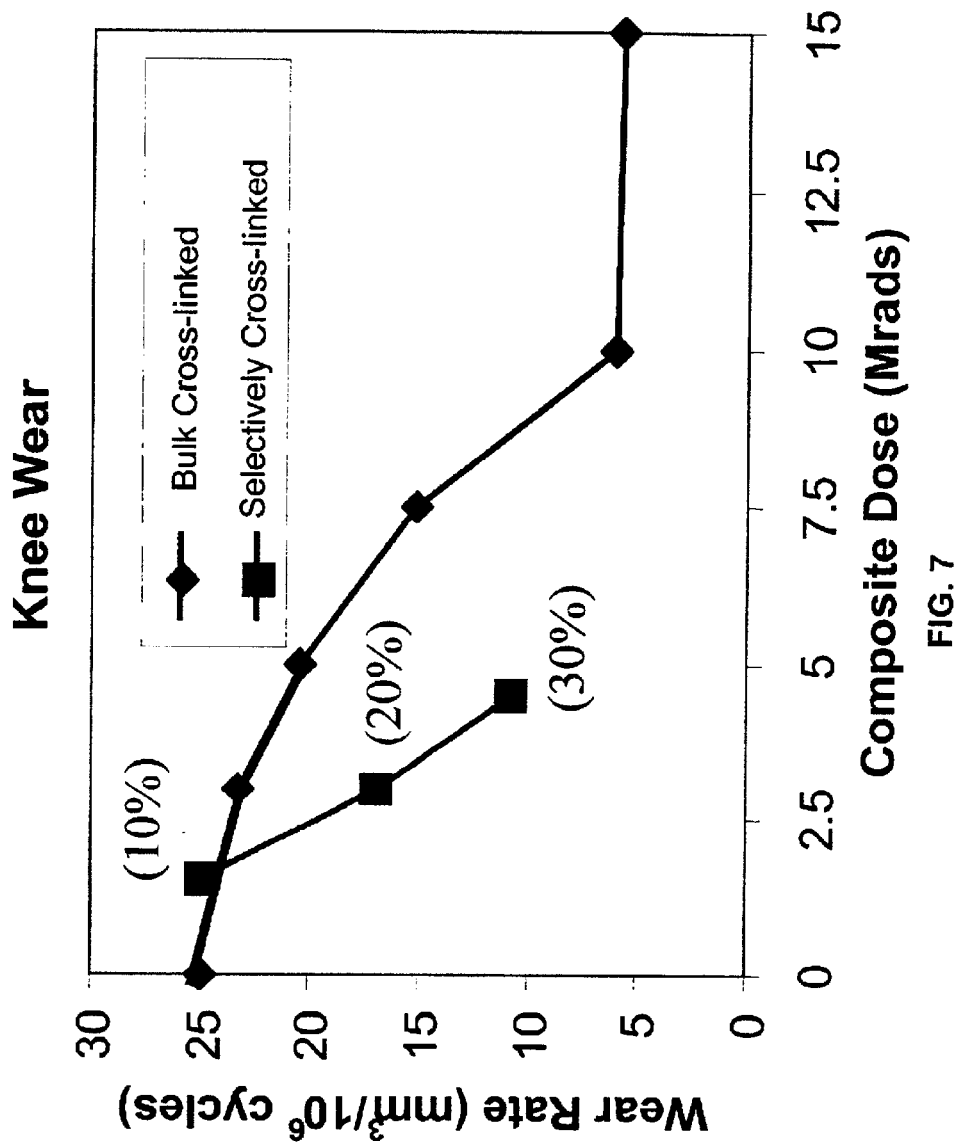
FIG. 7 depicts a representation of knee wear rate versus radiation composite dose equivalent dose.

The effect of the radiation dose on wear rate according to the present invention is illustrated in FIG. 6. As shown FIG. 6 demonstrates that the wear rate decreases along with the percent cross-linking at two radiation dose levels, 15 and 7.5 Mrads. FIG. 7 illustrates a comparison between conventional bulk cross-linking versus the selective cross-linking of the present invention. This is shown as a function of "composite dose" (cross-linking) in FIG. 7. The composite dose equals the percent cross-linking region multiplied by the dose received. For example, 30% of the cross-linked region is multiplied by the total dose received (15 Mrads), resulting in a composite dose of 4.5 Mrads; (0.30×15=4.5).

Figure 2:
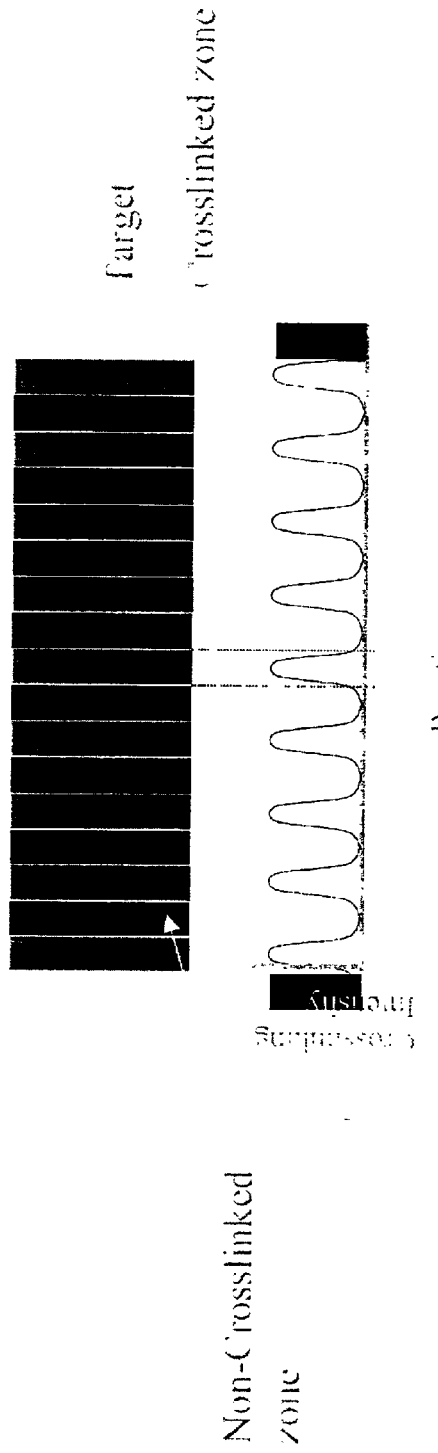
FIG. 2 depicts a representation of the path of an interrupted irradiation beam and the cross-linked zones created by the irradiation in the polyethylene workpiece. The distribution of the cross-linking within the zone is also demonstrated.

Without being limited to any particular theory to explain why or how the present invention works, the improved properties exhibited by the devices provided by the present invention may be explained as follows. The interrupting means causes specific and perhaps alternating zones of cross-linked and non cross-linked polymer to form within the matrix of the article exposed to the invention. As illustrated in FIG. 2, each cross-linked zone may possess a natural distribution of cross-linked polymer after exposure. As such, the post-exposure article could be composed of alternating zones of essentially two or more different polymers (by different we mean different cross-linking percentages) made so by the interrupted irradiation.

These different polymers may separately contribute to the overall physical properties of the resulting polymeric article. For example, the highly cross-linked zones may possess a high degree of strength, as is typically seen from most cross-linked polymers. A non cross-linked zone, may contribute a certain degree of pliability and flexibility. Because the different polymers are integrally networked within the polymer, a synergistically improved material results possessing many desirable properties such as wear resistance and toughness, without the undesirable aspects either of such properties normally includes when only individually present.

Another possible theory for the unexpected results of the present invention is set forth as follows. In a polymer matrix made according to the present invention whereby alternating cross-linked and non cross-linked zones have been formed, the non cross-linked zones exhibit a minor surface compression phenomenon whereby the termini of each non cross-linked zone depresses within the matrix due to its more pliable nature. The termini of the cross-linked zones, however, would not be as flexible or compressible, and therefore would not compress. If this is correct, the surface of a prosthetic joint made according to the present invention would in effect allow objects pressed to its surface to "ride" on a series of undulating cross-linked termini not unlike a series ball bearings. As such, less surface contact by an abutting bone or another prosthetic joint is made thereby minimizing the wear rate of the prosthetic device. The above described contact of undulated surfaces may also facilitate fluid entrapment and thus enhance lubrication. This proposed surface phenomenon could provide significant wear reduction to the limited overall surface contacted, but retain structural integrity.

DETAILED DESCRIPTION OF THE PREFERRED EMBODIMENTS

In one embodiment of the present invention, the polymer utilized to make up the prosthetic device or work piece may be selected from the group of polyethylenes including, but not limited to, high molecular weight polyethylene (HMWPE), ultra high molecular weight polyethylene (UHMWPE), high density polyethylene (HDPE), ultra high density polyethylene (UHDPE), cross-linked polyethylene and non-cross-linked polyethylene. The preferred polyethylene species of the present invention is UHMWPE. However, combinations of any or all of the above listed polymers, along with any equivalent polymer, may be combined to practice the present invention. The UHMWPE used in the present invention may preferably have a molecular weight between about 1,000,000 to about 10,000,000, in a more preferred embodiment, the molecular weight is between about 2,000,000 and 6,000,000. The HDPE used in the present invention may preferably have a molecular weight between about 1,000 to 1,000,000. In an even more preferred embodiment, the molecular weight is between about 200,000 to 500,000.

In another embodiment of the present invention, a desirable balance of toughness and wear rate in polyethylene is achieved when the cross-linking percentage is within the range of between about 1–90% selectively cross-linked. In a preferred embodiment of the present invention, the selectively cross-linked percentage is between about 1–50%. In a more preferred embodiment of the present invention, the selectively cross-linked percentage is between about 2.5–50%. In another preferred embodiment, the selectively cross-linked percentage is between about 2.5–40%. Even more preferred is a selectively cross-linked range of between about 5 to 30%, as illustrated in FIG. 1. Of course, this range may differ depending upon the particular device and its size, shape and intended use as well as the type of polyethylene comprising the device.

Another embodiment of the present invention provides for the mixture of polyethylenes. One particularly preferred embodiment includes a mixture of HDPE and UHMWPE. A preferred ratio of HDPE to UHMWPE is 50:50, and even more preferred ratio is 60:40, and the most preferred ratio is 70:30 HDPE to UHMWPE. This particular blend of polyethylenes exhibits unexpectedly favorable flow properties conducive to injection molding. A prosthetic device fabricated via injection molding and subjected to selective cross-linking, according to the present invention, provides an economically beneficial alternative to a more elaborate multi-step process requiring machining and finishing an extruded stock bar or rod.

Generally, the selective or controlled cross-linking of the present invention is accomplished by interrupting the exposure of the device to the irradiated beam. Several methods and devices may be employed to interrupt the irradiation beam. The irradiation may be fully or partially interrupted or intermittently interrupted in order to control exposure and dosage. The direction of any irradiation may also be controlled by employing a variety of methods and devices described below. The number of irradiation beams used on a particular device may also be varied so that a plurality of beams are simultaneously exposing, and therefore cross-linking, the polymeric matrix of the device.

Figure 12:
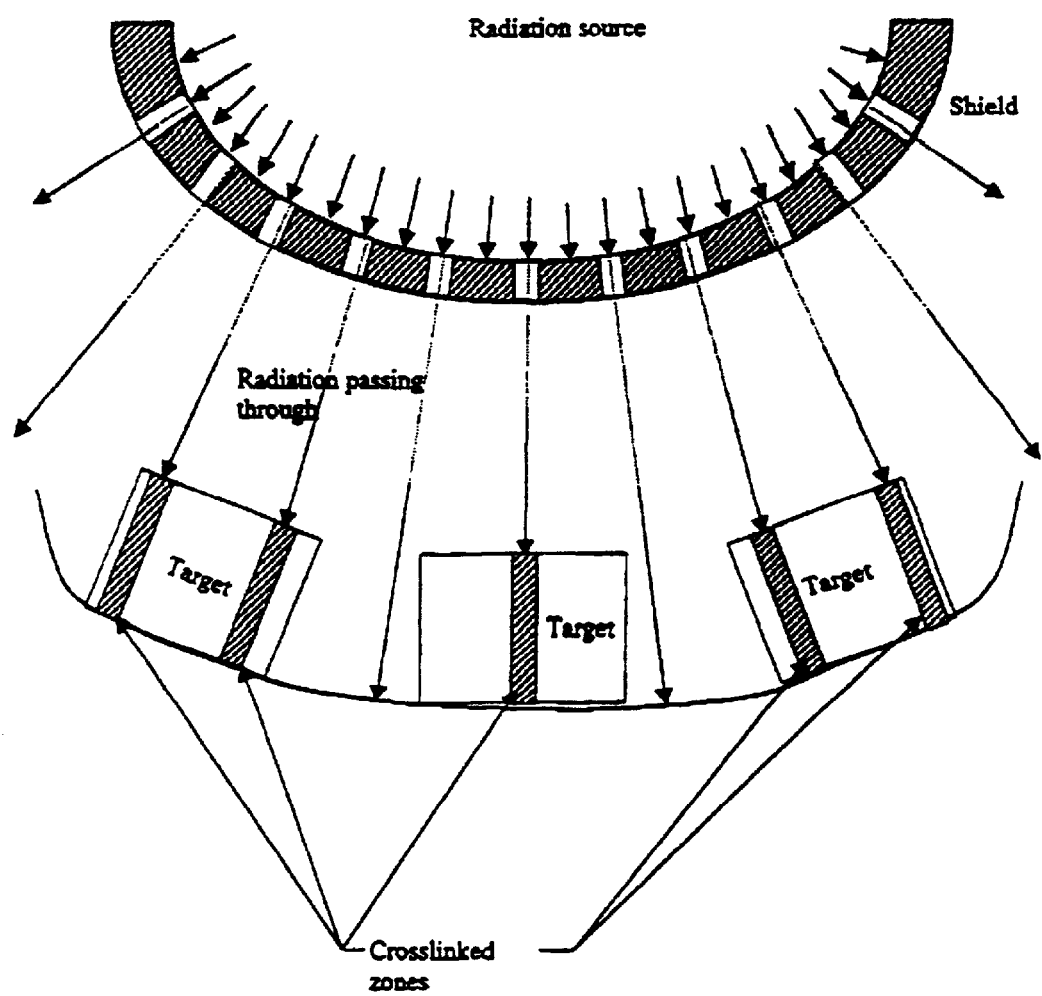
FIG. 12 depicts the use of a curved perforated mask used to irradiate a workpiece.

One such method employs a perforated mask or shield placed partially or fully between the irradiation source and the polyethylene object. (See FIGS. 2, 9, 11 and 12) The use of the perforated mask allows only certain zones of the polymer to become cross-linked. The zones that are not exposed to the irradiation do not become cross-linked. The perforated mask may be flat or curved to allow for the desired angle of inflection of the irradiation beam on the article being cross-linked (See FIGS. 9 and 12, respectively).

Another method of the present invention of interrupting the irradiation during the cross-linking process is to place a propeller or chopper wheel in between the irradiation source and the article being irradiated. An additional step to effectuate a synchronized translation or rotation of either the article or the irradiation source may also be performed concurrently with the propeller or chopper wheel interrupting step. These methods also provide for a controlled amount of irradiation to be exposed on the article in a pre-arranged pattern. The result is a selectively cross-linked article having the desired properties described above.

Yet another embodiment of the present invention provides a method of interrupting the irradiation by pulsing the energy from the irradiation source. An additional step to effectuate a synchronized translation of either the article or the irradiation source may also be performed may also be performed concurrently with the interrupting step. These methods also provide for a controlled amount of irradiation to be exposed on the article in a prearranged pattern. The result is a selectively cross-linked article having the desired properties described above.

Figure 10:
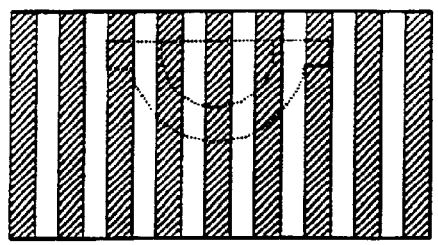
FIG. 10 depicts selectively cross-linked patterns formed within and around a polymer workpiece with and without rotation.
Figure 10:
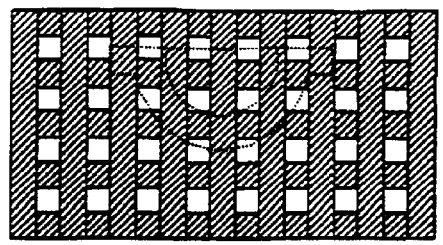
Figure 10:
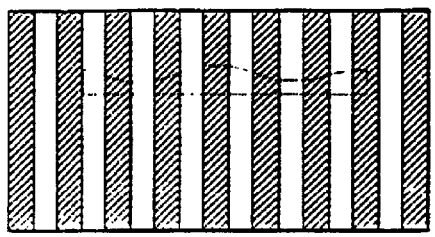
Figure 10:
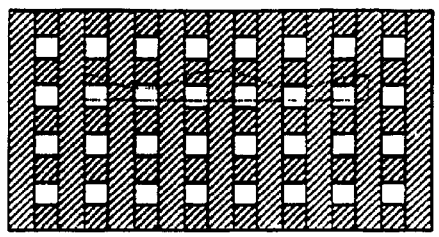
Figure 10:
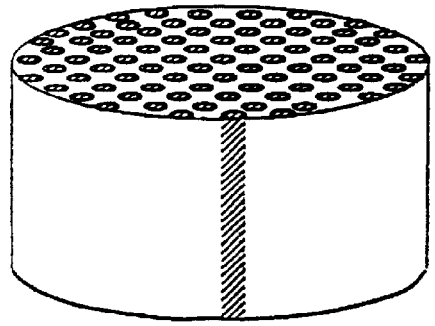
Figure 10:
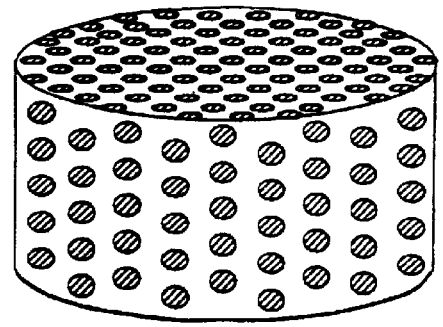
Figure 11:
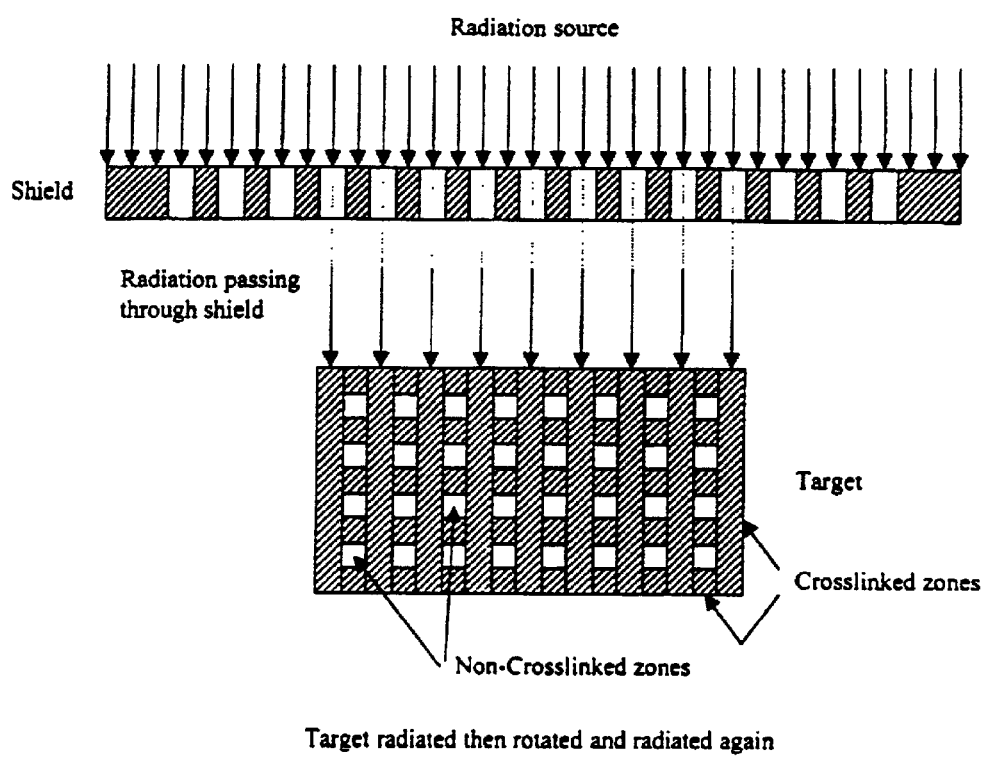
FIG. 11 depicts selectively cross-linked patterns formed by rotation of the workpiece.

In still another embodiment of the invention, the article being cross-linked can be translated, rotated, vibrated, etc., during or in between the irradiation step or steps in order to control exposure, dosage and directionality of the irradiation on the article. Such control may be desirable depending upon the ultimate use of the article. For example, an article may be first exposed to an interrupted irradiation beam to produce a selectively cross-linked pattern in a particular direction. The article may then be rotated so that when the irradiation source is resumed, the exposure of the interrupted beam creates a selectively cross-linked pattern in another direction. The end result would be for example a cross-hatched pattern of cross-linked zones within and on the surface of the workpiece, including the joint or limb bearing surface of the workpiece. See FIGS. 10 and 11. As shown in FIG. 10, at least portions of the joint or limb bearing surface area are cross-linked and adjacent portions of the bearing surface area are not cross-linked. This method may be termed multi-directional selective cross-linking. Such a process would render the article useful in applications where a multi-directional array of force is imposed on the article, e.g., in an acetabular cup or liner component of a hip joint replacement prosthesis as shown in FIG. 10.

In another embodiment the workpiece or pre-formed medical device may be vibrated while being subjected to selective cross-linking through any of the methods described herein.

In another embodiment of the invention, the device to be selectively cross-linked is positioned inside a perforated housing and exposed to at least one irradiation source. Where a plurality of irradiation sources is used, the device is exposed to irradiation in multiple directions.

The following embodiments are intended to illustrate the capability of the selective cross-linking invention. The methods so described are illustrative only and should not be interpreted as constituting any limitations on the methods in accordance with the present invention.

In one embodiment, a polyethylene workpiece or orthopedic implant preform is irradiated in such a way that portions of the workpiece or orthopedic implant preform are not cross-linked. In one aspect of this embodiment, the irradiation source is fully or partially interrupted or intermittently interrupted.

In a preferred embodiment of the invention a seven step process is employed to selectively cross-link a polyethylene workpiece. In the first step, a polyethylene article comprised of UHMWPE in the form of a rod, bar, implant-preform or acetabular cup, tibial or patellar component is formed through molding, extrusion or other polymeric forming process.

The second step involves placing the polyethylene article under an irradiation source where an interrupting means such as a wire mesh, porous plate or other partial masking device has been placed between the irradiation source and the polyethylene component. The interrupting means is perforated so that about 30% of the irradiated energy passes through it and thus contacts the article.

Step three involves irradiating the component at a suitable accumulated dose between the range of about 2.5 and 100 Mrads, preferably at about 5 to 15 Mrads. A preferred composite dose is between about 1 to 25 Mrads. Additional preferred composite doses are between about 5 to 25 Mrads and about 10 to 20 Mrads. An even more preferred composite dose is between about 2 to 10 Mrads, with the most preferred composite dose being about 4.5 Mrads. The irradiation source may be for example gamma rays, x-rays, electron beam or other radiation source. The duration of irradiation exposure is carried out for an appropriate time, depending upon the dose rate and the desired total dose. For example, a calibration curve may be generated plotting exposure time or dose rate versus wear rate for a particular shaped article or workpiece. Thereafter, to determine the dose rate or exposure time to obtain a desired level of wear rate, one need only refer to the calibration curve for the appropriate parameters.

Step four involves annealing the irradiated component at an elevated temperature (below, at, or above the melting point, of polyethylene). The fifth step involves machining the irradiated component if necessary into its final shape for implantation. The sixth step involves thoroughly cleaning the finished component and placing it in a sealed package. The package may be substantially free of free oxygen and may be any container or expedient for creating and maintaining a low or zero oxygen environment. Step seven involves sterilizing the packaged component with gamma, gas-plasma or ethylene oxide. In the case of ethylene oxide, the gas may be introduced in the packaging step six.

In another embodiment of the invention, a method for the production of a multi-directional cross-linked article is employed. For example, such a method comprises the method of creating multi-directional irradiation zones by exposing the article to an interrupted irradiation beam in one direction, then relocating either the irradiation beam or the article to another position than the first irradiation direction, then exposing the article to the second irradiation exposure. See FIGS. 10 and 11. The repositioning step may be performed a plurality of times. An article that has been multi-directionally irradiated possesses isotropic physical properties, and is desirable for example for use as a prosthetic implant requiring multi-directional loading strength.

In yet another embodiment of the present invention, a polymer blend of HDPE and UHMWPE is combined and injection molded into a prosthetic device. The device is then subjected to any of the selective cross-linking methods discussed above. In a preferred embodiment, a ratio of 50:50 HDPE to UHMWPE is blended and injection molded according to conventional methods known in the art. In an even more preferred embodiment, a blend of 60:40 HDPE to UHMWPE is used, and most preferred is a blend of 70:30 HDPE to UHMWPE.

EXAMPLE

Several shields were produced from a 3/8 inch thick steel plate for selective cross-linking treatment of UHMWPE. The overall top surface size for each plate was approximately 5 inches by 5 inches square. Each shield was perforated with a series of 3 mm diameter holes in a geometric arrangement such that each perforation (hole) was equally spaced from all other perforations. One pattern involved 30% porosity or perforation. That is, 30% of the top surface area of the shield was occupied by holes uniformly distributed over the surface of the shield. These parameters (3 mm hole size, equal spacing and 30% surface area) control the total number of holes as well as the inter-hole spacing. An additional shield used a 20% surface area pattern and a third used a 10% pattern.

A 3.25 inch diameter cylindrical rod of UHMWPE material was sectioned into 1.75 inch thick pieces or "pucks". This rod was made of GUR 1050 resin and was not treated or cross-linked in any way. This is typically referred to as "virgin" rod. The 1.75 inch height was selected to allow uniform cross-linking through the entire thickness (height) of the puck. These pucks were then selectively cross-linked using the description that follows. See FIG. 8.

An electron beam was used to provide ionizing radiation to cross-link the UHMWPE material. This process involved exposing an UHMWPE puck to the electron beam until the desired energy was projected onto the puck. Prior to irradiation, a perforated shield was placed between the electron beam source and the UHMWPE puck such that only the areas of the puck not covered by the shield received electron beam energy. In this way the UHMWPE puck was selectively cross-linked. See FIG. 9. The parameters used for the electron beam treatment were an absorbed 10 MeV ionizing radiation dose of 150 kiloGrays (15Mrads) at a rate of 20 kiloGrays (2Mrads) per minute so that total treatment time was 7.5 minutes. Pucks were treated using the 10%, 20% and 30% perforation shields. These pucks were then heat treated or annealed. After this step the pucks were then manufactured into knee replacement tibial inserts as well as tensile test specimens.

These tibial inserts were then tested in a knee wear simulator. This machines duplicates the motions and loading seen in a knee joint during normal walking activity. Appropriate physiological conditions were used. Results in FIG. 4 show that selective cross-linking improves wear resistance over the untreated control. Details of the perforated pattern used influence performance. The tensile specimens were tested in a load frame device to yield mechanical property values, such as strength and elongation. See FIGS. 3 and 5. These values also change with the pattern. Unlike wear, it is desirable to keep these values high.

It is therefore intended that the foregoing detailed description be regarded as illustrative rather than limiting, and that it be understood that it is the following claims, including all equivalents, which are intended to define the scope of the present invention.

We claim:

1. A method of preparing an orthopedic prosthetic medical device having a joint or limb bearing surface, comprising the steps of:

providing a preformed orthopedic polyethylene device; and enclosing the device in a package to provide a low oxygen content environment; and positioning at least one irradiation source adjacent to the packaged device so that the packaged device may be exposed to irradiation from the irradiation source; and interrupting the irradiation source so that at least portions of the orthopedic prosthetic joint or limb bearing surface are cross-linked and adjacent portions of the orthopedic prosthetic joint or limb bearing surface are not cross-linked.

2. The method of claim 1, further comprising the step of translating the packaged device.

3. The method of claim 1, further comprising the step of arranging a perforated mask between the irradiation source and the packaged device.

4. The method of claim 1, further comprising the step of arranging a wire mesh between the irradiation source and the packaged device.

5. The method of claim 3, wherein the perforated mask is curved.

6. The method of claim 4, wherein the wire mesh is curved.

7. The method of claim 1, further comprising the step of positioning a rotatably mounted chopper wheel between the irradiation source and the packaged device.

8. The method of claim 1, further comprising the step of pulsing the irradiation source.

9. The method of claim 1, wherein the irradiation step is controlled to deliver a dose of irradiation between 2.5 and 100 Mrads.

10. The method of claim 1, wherein the composition of the orthopedic prosthetic medical device is selected from the group consisting of high molecular weight polyethylene, ultra high molecular weight polyethylene, high density polyethylene, ultra high density polyethylene, cross-linked polyethylene and non-cross-linked polyethylene.

11. The method of claim 1, wherein the irradiation step is controlled to deliver a dose of irradiation between about 5 to 25 Mrads.

12. The method of claim 1, wherein the irradiation step is controlled to deliver a dose of irradiation between about 10 to 20 Mrads.

13. The method of claim 1, wherein the steps effectuate cross-lnking of a selected pattern on the joint or limb bearing surface.

14. The method of claim 13, wherein the selected pattern comprises a cross-hatched pattern of cross-linked and non-cross-linked zones.

15. The method o claim 1, wherein the steps effectuate cross-lnking of a selected percentage of surface area on the device.

16. The method of claim 15, wherein the selected percentage of cross-linking is within a range of between about 1 to 90%.

17. The method of claim 15, wherein the selected percentage of cross-linking is within in a range of between 1 to 50%.

18. The method of claim 15, wherein the selected percentage of cross-linking is within a range of between about 2.5 to 50%.

19. The method of claim 15, wherein the selected percentage of cross-linking is within in a range of between 2.5 to 40%.

20. The method of claim 15, wherein the selected percentage of cross-linking is within a range of between about 5 to 30%.

* * * * *

UNITED STATES PATENT AND TRADEMARK OFFICE
CERTIFICATE OF CORRECTION

PATENT NO.     : 6,849,224 B2
DATED          : February 1, 2005
INVENTOR(S)    : Aiguo Wang, Aaron Paul Essner and Alfred J. Zarnowski It is certified that error appears in the above-identified patent and that said Letters Patent is hereby corrected as shown below:

Column 2,
Line 41, after "invention" insert -- , --.

Column 3,
Line 6, after "may" insert -- be --.

Column 5,
Line 45, after "example" insert -- , --.
Line 67, after "shown" insert -- , --.

Column 6,
Line 28, after "zone" delete ",".

Column 8,
Line 30, after "be" insert -- , --.
Line 30, after "example" insert -- , --.

Column 9,
Line 16, after "be" insert -- , --.
Line 16, after "example" insert -- , --.
Line 29, after "component" insert -- , -- and after "necessary" insert -- , --.

Column 10,
Line 37, "machines" should read -- machine --.

Column 12,
Lines 17 and 23, after "within" delete "in".

Signed and Sealed this

Twenty-fourth Day of May, 2005

JON W. DUDAS
*Director of the United States Patent and Trademark Office*